(12) United States Patent
Maksimovich

(10) Patent No.: US 7,389,776 B2
(45) Date of Patent: Jun. 24, 2008

(54) METHOD AND DEVICE FOR ENDOVASCULAR TREATMENT OF THE ALZHEIMER'S DISEASE

(76) Inventor: Ivan Vasilievich Maksimovich, Russian Federation, 121248, 4/2 Moscow, Kutuzovsky Prospect, Apt. 121, Moscow (RU)

( * ) Notice: Subject to any disclaimer, the term of this patent is extended or adjusted under 35 U.S.C. 154(b) by 31 days.

(21) Appl. No.: 11/650,364

(22) Filed: Jan. 8, 2007

(65) Prior Publication Data

US 2007/0185476 A1    Aug. 9, 2007

(30) Foreign Application Priority Data

Feb. 7, 2006    (RU)    ............................... 2006103318

(51) Int. Cl.
*A61B 19/00*    (2006.01)
(52) U.S. Cl. .......................................... 128/898; 606/15
(58) Field of Classification Search ................. 128/898; 607/7, 10–18, 88, 89, 92; 604/164.01, 171, 604/174

See application file for complete search history.

(56) References Cited

U.S. PATENT DOCUMENTS

| | | | |
|---|---|---|---|
| 5,236,942 A | | 8/1993 | Miller |
| 5,846,220 A | * | 12/1998 | Elsberry ..................... 604/500 |
| 5,895,378 A | * | 4/1999 | Nita ........................... 604/529 |
| 6,272,370 B1 | * | 8/2001 | Gillies et al. ................ 600/411 |
| 7,048,719 B1 | | 5/2006 | Monetti |
| 7,153,292 B2 | * | 12/2006 | Morris et al. ............... 604/246 |
| 7,189,222 B2 | * | 3/2007 | Elsberry ..................... 604/506 |

OTHER PUBLICATIONS

The use of donepezil for treating psychotropic-induced memory loss; by Jacobsen, F. M. and Comas-Diaz, L. in (http://cat.inist.fr/?aModele=afficheN&cpsidt=1997195).

Genetically modified tissue surgically implanted into the brain of an Alzheimer's patient (University of California, San Diego (UCSD) School of Medicine) (http://health.ucsd.edu/news/2001/04_09_Tusz.html).

Neurologists at Emory University (Atlanta, Georgia, USA) are studying a possible new treatment for Alzheimer's disease using a device called the COGNIShunt. http://www.sciencedaily.com/releases/2002/03/020327073547.htm.

* cited by examiner

*Primary Examiner*—Ahmed M Farah

(57) ABSTRACT

A method of treating patients suffering from Alzheimer's disease by locating the areas of the brain affected by Alzheimer's disease and acting on the aforementioned areas of the patient's brain by laser energy through coronary blood vessels located adjacent to the aforementioned areas. The laser energy is delivered to the affected area through a set of microcatheters insertable sequentially and coaxially into each other and having diameters that allow insertion into distal coronary blood vessels.

17 Claims, 2 Drawing Sheets

METHOD AND DEVICE FOR ENDOVASCULAR TREATMENT OF THE ALZHEIMER'S DISEASE

FIELD OF THE INVENTION

The present invention relates to the field of medicine, in particular to neuroangiologia. More specifically, the invention relates to a method and device for treating the Alzheimer's disease.

BACKGROUND OF THE INVENTION

In recent years the number of cases of Alzheimer's disease has noticeably increased, and according to the forecast of scientists, the number of people suffering from this disease may reach 50 million in near decades.

Alzheimer's disease is one of most widely spread forms of acquired dementia that affects the population of developed countries. In the USA alone the number of people suffering from this disease is about 4.5 million, and it is very difficult to diagnose this disease in its early stage.

Alzheimer's disease is a degenerative disease of the brain that manifests itself in progressive loss of memory and intellect and, in the long run, leads to complete degradation of personality. Until the present time, etiology of this disease has not been completely known, and it is not infrequent that this disease has an inheritable nature.

In the Alzheimer's disease, main structural changes are revealed in the surface structures of the brain (cerebral brain cortex) and in the hippocampus, which is located in the depth of the hemispheres and plays an important role in memory and processes of memorization. Microscopic observations show that these changes are characterized by the presence of so-called neurofibrillar glomerules that consist of pathologically changed neurons (nerve cells) that contain specific fibrillar proteins and neuritic plaques that comprise deposits of amyloids, i.e., protein-hydrocarbon complexes, in an intercellular space of the brain. At the same time, one can observe a reduction of the capillary bloodstream in the frontoparietal part with development of multiple arteriovenous shunts.

At the present time Alzheimer's diseases is treated mainly by symptomatic methods based on introduction of acetylcholine and psycotropic preparations designed for correcting behavioristic deviations.

At the present time, Alzheimer's disease is treated mainly on the basis of symptomatic methods relating to introduction of acetylcholine and psycotropic preparations designed for correcting behavioristic deviations. For example, an article by Jacobsen, F. M. and Comas-Diaz, L. in (http://cat.inist.fr/?aModele=afficheN&cpsidt=1997195) describes the use of donepezil for treating psychotropic-induced memory loss. Donepezil is an acetylcholinesterase inhibitor marketed for treatment of memory loss and behavioral deterioration associated with the acetylcholine deficit of Alzheimer's disease. The authors investigated the utility and tolerability of donepezil in nongeriatric-affective illness for treatment of psychotropic-induced memory loss, dry mouth, and constipation. Nondemented outpatients with stabilized DSM-IV-affective illness took 5 mg/day of donepezil for three weeks and then increased to 10 mg/day in open trials. Self-rating scales of target symptoms were completed by patients before and three to four weeks after starting each dose. Patients who chose to continue donepezil therapy returned for clinical monitoring every four to eight weeks. Results showed that 11 women and 11 men (mean±SD age=45.4±8.5 years) completed donepezil trials. Nineteen patients with memory loss rated improvement while taking 5 mg/day of donepezil (p<0.001); subsequently, six patients rated further improvement with 10 mg/day (p=0.057). Donepezil, 5 mg/day, also reduced ratings of dry mouth (N=16; p<0.001) and constipation (N=11; p<0.05). Side effects included insomnia, nausea, vomiting, and diarrhea; surprisingly, two bipolar patients became manic within hours of starting donepezil. Sixteen patients (72%) continued donepezil for an average of seven months. Consideration of family histories suggested that donepezil response in affective illness may be an early indicator of vulnerability to dementia of the Alzheimer's type.

However, even though donepezil can reduce memory loss, dry mouth, and constipation in nongeriatric-affective patients, the authors, themselves, state that use of this preparation may trigger mania and may have other side effects.

Physicians at the University of California, San Diego (UCSD) School of Medicine have surgically implanted genetically modified tissue into the brain of an Alzheimer's patient. This launches the first phase of an experimental gene therapy protocol for Alzheimer's disease. The 11-hour procedure was performed at UCSD's John M. and Sally B. Thornton Hospital in La Jolla on a 60-year-old woman in the early stages of Alzheimer's disease. The authors reported that the patient was recovering well. The authors also stated that the proposed gene therapy is not expected to cure Alzheimer's disease, but they hope that it might protect and even restore certain brain cells and alleviate some symptoms, such as short-term memory loss, for a period that could last a few years. This procedure targets a class of cells located deep within the brain in an area called the cholinergic system, important for supporting memory and cognitive function.

The cholinergic system profoundly degenerates in the course of Alzheimer's disease. These cells have been shown to respond to the implanted genetically modified tissue in primate studies, and the researchers hope that preventing extensive loss of these cells may slow intellectual decline seen in Alzheimer's patients.

Also known in the art are some other surgical methods for treating Alzheimer's disease. For example, neurologists at Emory University (Atlanta, Ga., USA) are studying a possible new treatment for Alzheimer's disease using a device called the COGNIShunt, which is designed to drain cerebrospinal fluid (CSF) from the skull into the abdominal cavity. Doctors are hopeful that by reducing the buildup of CSF around the brain, this device will help to stabilize the disease.

CSF is the fluid that fills the empty spaces around the brain and spinal cord. The body naturally produces, absorbs, drains, and replenishes the fluid; however, with age, the replenishing process slows. Shunting has long been used as treatment for hydrocephalus, a condition in which an abnormal accumulation of CSF causes neurological problems, including dementia, problems walking, and incontinence. In the Emory study, surgeons surgically implant the COGNIShunt into a normal cavity, or ventricle, in the brain. Then they tunnel a tube through the neck and into the abdominal cavity for proper drainage. This procedure is a relatively short and common procedure that usually requires a one- to two-day hospital stay. However, the results of this study are yet unknown, and there are some risks associated with implanting the device. The risks include infections, bleeding, or a chance that the shunt or tube could stop working.

On the other hand, known in the art is the use of endovascular catheters for internal treatment of patients suffering from vascular disorders. For example, U.S. Pat. No. 7,048,719 issued in 2006 to Richard R. Monetti discloses the use of endovascular microcatheters to deliver embolic devices useful in occluding blood flow through a patient's vasculature. Blood flow occlusion may be useful in controlling vascular bleeding, controlling blood supply to tumors, and to occlude vascular aneurysms, including intracranial aneurysms. Microcatheters can be used when treating blood vessels of extremely small size, for example, intracranial blood vessels. In particular, the aforementioned patent discloses a resheathing apparatus useable to resheath an elongate member such as a catheter, embolization member deployment apparatus, or other elongate structure. The resheathing apparatus comprises a guide that has one or more lumens extending from the proximal end to the distal end of the guide. The guide also may have a branch extending away from the lumen of the guide. The branch is structured to fit in a sheath that may be disposed around the deployment structure. The branch is oriented to direct the sheath onto or off the deployment structure, depending on whether the deployment structure is to be resheathed or desheathed, respectively. The resheathing apparatus may also comprise a guide tube disposed over the branch of the guide to facilitate movement of the sheath over the branch of the guide and over the deployment structure.

The endovascular catheter of the type shown in the above patent can be used for angioplasty and for delivery of embolic devices useful in occluding blood flow through a patient's vasculature. Blood flow occlusion may be useful in controlling vascular bleeding, controlling blood supply to tumors, and to occlude vascular aneurysms, including intracranial aneurysms. Microcatheters can be employed when treating blood vessels of extremely small size, for example, intracranial blood vessels.

In spite of all known attempts aimed at treating Alzheimer's disease and attempts as described above, the inventor herein is not aware of surgical methods and devices for treating this disease based on restoring surrounding brain tissue by improving microcirculation and collateral bloodstreams in the brain.

OBJECTS AND SUMMARY OF THE INVENTION

It is an object of the present invention to provide a surgical method and apparatus for treating the Alzheimer's disease by restoring the microcirculation and collateral bloodstreams in the brain with regeneration of the surrounding brain tissue. It is a further object to carry out the above method by means of a coaxial multi-catheter device and with the use of laser technique. It is another object to provide a unique microcatheter-type apparatus consisting of 3 or more coaxially assembled microcatheters for treating Alzheimer's disease by restoring the microcirculation and collateral bloodstreams in the brain with regeneration of the surrounding brain tissue due to the use of laser therapy.

The method of the invention consists of the following steps: conducting pre-operative examination of a patient suffering from Alzheimer's disease including such procedures as computerized and magnetic resonance tomography of the brain, scintography, rheography, etc., and defining angioarchitechtonica of the arteries and capillaries in the affected zone of the brain; preparing a microcatheter or a set consisting of a plurality (three or more, up to six) of microcatheters for sequential coaxial insertion one into another and for guiding though the intracranial blood vessels to the affected zone; if necessary, modifying the distal tips of the catheters of the set in accordance with the shape of specific curves in the angioarchitectonica of the brain of the patient who is to be treated; conducting puncturing and catheterization for installing an introducer, e.g., into the common femoral artery; sequentially inserting one, two, or more microcatheters of the aforementioned set until the affected portion of the microcirculation bloodstream in the patient's brain is reached; inserting a light-guiding optical-fiber device coaxially into the innermost catheter; guiding the optic-fiber device to the affected zone through the innermost catheter; and conducting laser treatment of the affected zone with a low-energy laser operating in a selected continuous, pulsed, or a combined continuous-pulsed mode. The catheters are made radio opaque and the entire surgical intervention is carried out under constant X-ray TV observation. Laser treatment is accompanied by introduction of a heparinizated physiological solution. After the installation of the light-guiding optical-fiber laser device is completed, the outermost guiding catheter is shifted and positioned in the descending arch of the aorta, and the inner catheter or catheters is/are shifted and positioned in the proximal part of the common carotid artery. Following this, laser treatment is carried out with advancement of the light-guiding device along the blood vessel together with the lightguide. A radio-opaque substance is periodically introduced for X-ray TV control.

The device for carrying out the method comprises a conventional three-way microcatheter device having at its proximal end a three-way connection unit with one channel for coaxial insertion of microcatheters and a sealed lightguide insertable into the innermost catheter, and another channel for injection of a physiological solution. The device is provided with a plurality (normally, three to six) of individual catheters having gradually diminishing diameters for sequential coaxial insertion of one into the other. The individual microcatheters are unique in that their distal ends have a shape memory and are modified and tailored to specific and preliminarily determined angioarchitechtonica of the brain of the patient who is to be treated.

The solution is composed of at least 0.1 ED heparin. The rate of introduction is no less than 0.1 mk/sec. Such a solution is needed for constantly washing the distal end of the lightguide and for replacement of blood in the area of laser treatment.

After the installation of the light-guiding optical-fiber device is completed, the first guiding catheter is shifted to the proximal part of the common carotid artery for reducing possibility of closing the vessel passage. Following this, simultaneously with laser treatment, the lightguiding device together with the lightguide is moved forwards along the blood vessel. This stage of the operation is accompanied by periodic introduction of small doses of a radio-opaque substance required for X-ray TV control.

DETAILED DESCRIPTION OF THE INVENTION

Figure 1:
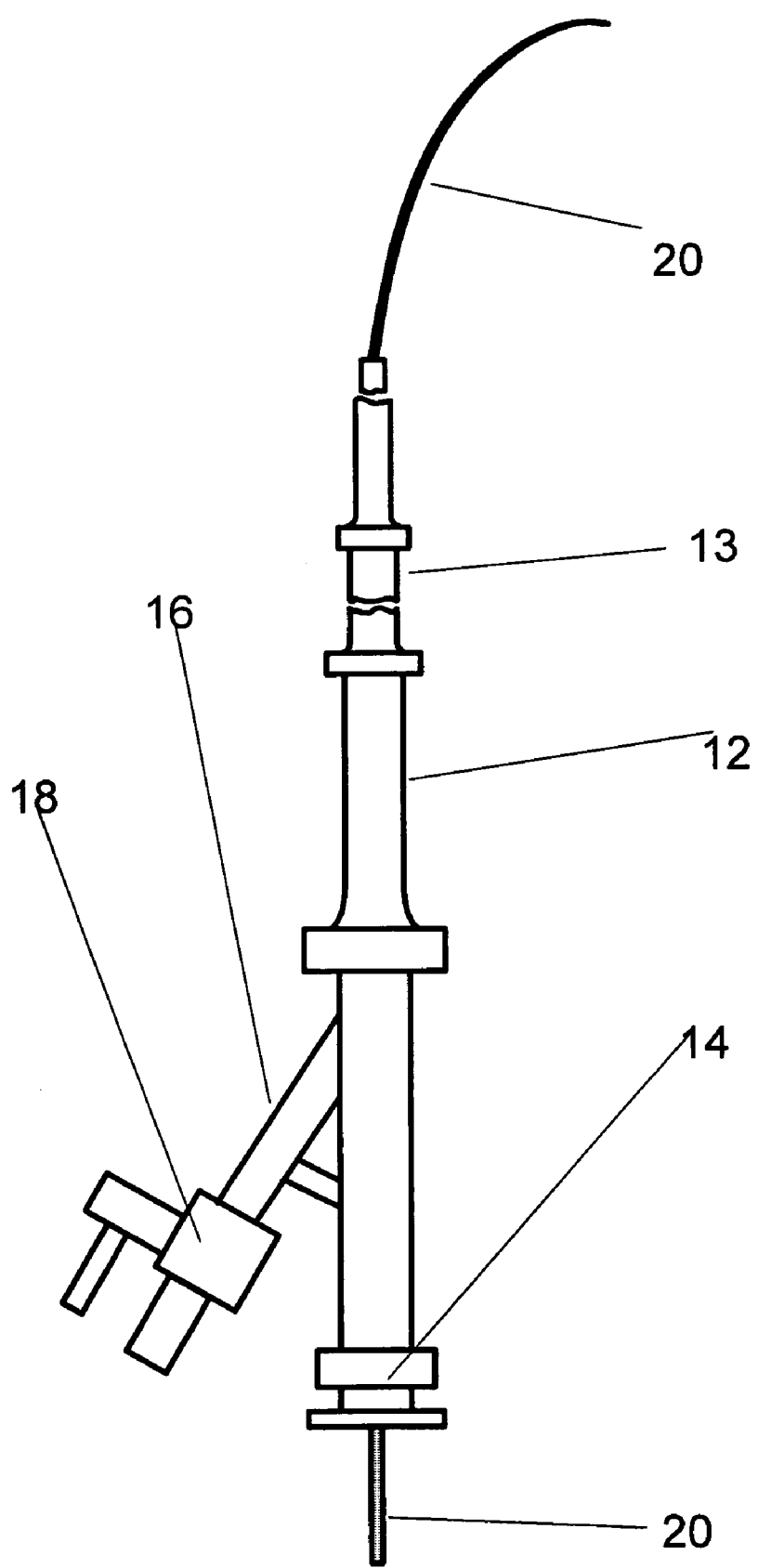
FIG. 1 is a general view of a three-way catheter device used for realization of the method of the invention.

Prior to surgical endovascular laser treatment, the patient is subjected to pre-operative examination. Such an examination may include computerized and magnetic resonance tomography of the brain, scintography, rheography, and brain angiography. The examination is aimed at revealing such disorders as involuntary changes accompanied by atrophy of the cerebral cortex in the frontal and parietal parts of the brain, abnormalities in the structure of the hippocampus, abnormalities in the blood circulation, abnormalities in pulse volume in the carotid sinuses, as well as reduction in the capillary phase of contrast enhancement in the frontoparietal areas with development of multiple arteriovenous shunts. If necessary, the investigation may also be carried out for defining angioarchitechtonica of the brain of the specific patient for preparing a set of microcatheters the distal ends of which may have a shape corresponding to the defined angioarchitechtonica.

The surgical endovascular method of the invention for treating the Alzheimer's disease begins with puncturing and catheterization of the common femoral artery by inserting an introducer having a diameter in the range of 6 to 9 F. Puncturing and catheterization are carried out under roentgenoscopy in accordance with the Seldinger's technique. This technique is based on introducing a catheter into a vessel via a needle puncture. The vessel is located with a special needle that contains a wire, and then the needle is removed. The catheter is threaded into the vein while being guided by the wire over which it is moving. The wire is then removed from the needle.

The first three-way type of guiding microcatheter is coaxially inserted through the introducer. This microcatheter comprises a thin-walled, radio-opaque, reinforced tube having a diameter of 5 to 8 F with a modulated distal part. The first microcatheter is selectively guided into the trunk of the internal carotid artery.

The first microcatheter is used for inserting a second modulated guiding microcatheter having a diameter of 4 to 5 F and then, in a super-selective manner, the second microcatheter, the third, and, if necessary, other smaller-diameter catheters are introduced (by sequentially and coaxially inserting one into the other) into the medial cerebral artery or the anterior cerebral artery. The innermost microcatheters, in turn, are used to insert a thin light-guiding optical-fiber device connected to a laser device for subsequent laser treatment. The aforementioned light-guiding optical-fiber device is guided to distal areas and to the affected portion of the microcirculation bloodstream.

The light-guiding optical-fiber device comprises a flexible radio-opaque catheter having a diameter of 2 F to 3.5 F F, the interior of which contains a movably installed flexible quartz-quartz type or quartz-polymer type of light-guide having an overall diameter in the range of 50 μm to 100 μm and an optical-fiber device having a diameter in the range of 50 to 100 μm.

The proximal end of the microcatheter is a three-way type end. One of two channels of this three-way connection is used for coaxial insertion of microcatheters and a sealed lightguide inserted into the innermost microcatheter, and another channel is used for connection to an injector of a washing liquid, e.g., a heparinizated physiological solution. Such a solution is composed of at least 0.1 ED heparin. The rate of introduction is no less than 0.1 mk/sec. The solution is needed for constantly washing the distal end of the lightguide and for replacement of blood in the area of laser treatment.

After the installation of the light-guiding optical-fiber device, the first guiding catheter is shifted to the proximal part of the common carotid artery for reducing possibility of closing the vessel passage. Following this, simultaneously with laser treatment, the lightguiding device together with the lightguide is moved forwards along the blood vessel. This stage of the operation is accompanied by periodic introduction of small doses of a radio-opaque substance required for X-ray TV control.

The laser treatment is carried out with the use of a low-energy laser that has the power not less than 20 mW and that operates either in a continuous, pulsed, or a combined continuous-pulsed mode.

Such laser treatment laser treatment affects the brain tissue that contains neurofibrillar glomerules and neuritic plaques and regenerates microcirculation and collateral bloodstreams in the brain.

After completion of the operative intervention, the patient is subjected to a repeated cerebral angiography, the results of which are used for evaluating a degree of regeneration of the blood passage through the microcirculation and collateral bloodstreams.

If the first attempt to restore blood circulation through the capillary vessels did not result in complete regeneration, the procedure is repeated.

If the results are successful, and the passage through the bloodstreams is completely restored, the catheter device and the introducer are removed, hemostasis is carried out, a compressive aseptic bandage is applied, and the patient is transferred to a post-operative ward under observation of medical staff, where EKG (electrocardiogram) and EEG (electroencephalogram) monitoring are performed. Subsequently, the conditions of the patient are checked via scintography and REG (rheography).

After a certain period of time, the patient is subjected to computerized and magnetic-resonance tomography, the results of which are used for evaluating regeneration of the brain-tissue structure.

The examples below illustrate the methods of the invention.

Figure 2:
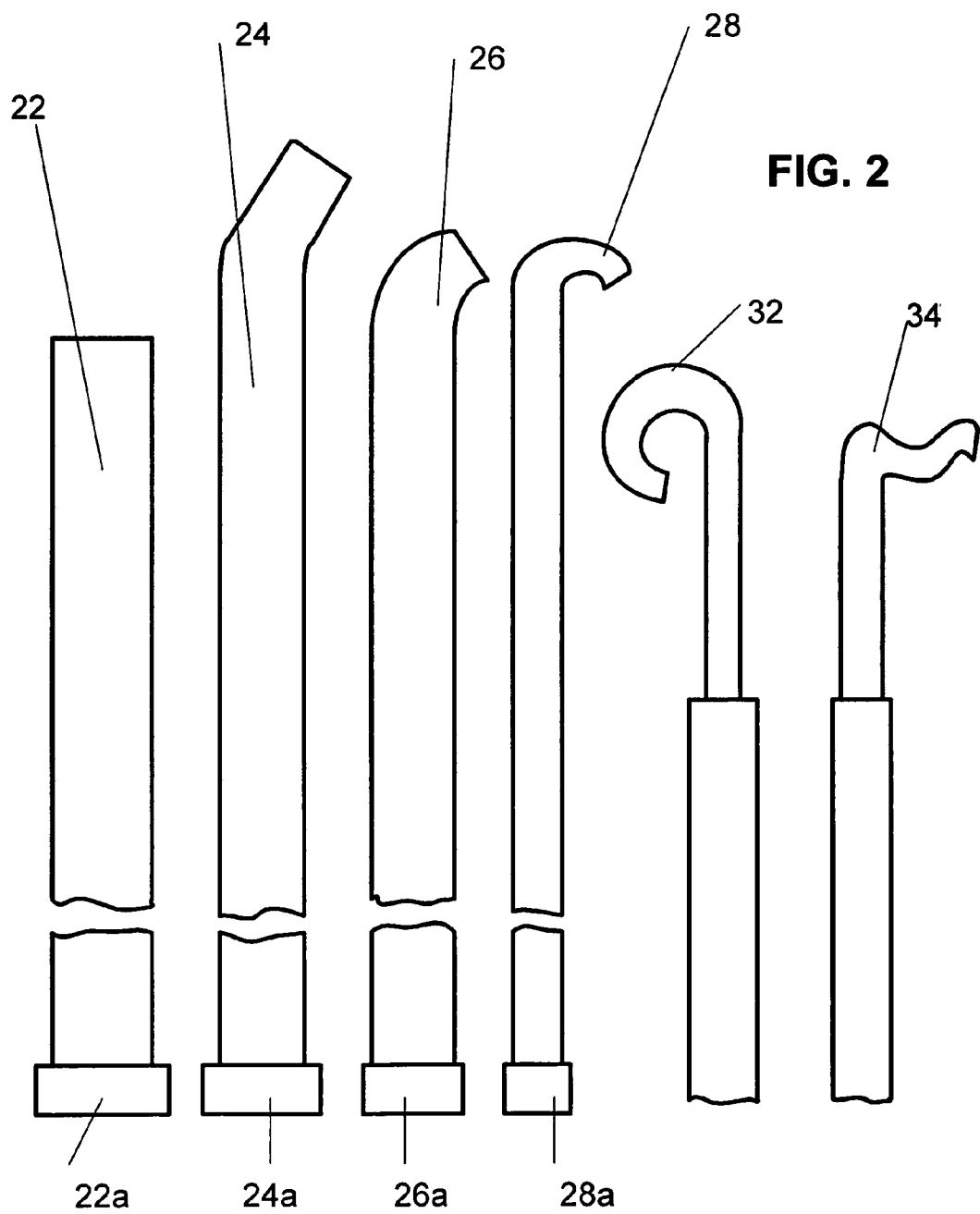
FIG. 2 is a view of a set of microcatheters for use with the device of FIG. 1 with some of the microcatheters having distal ends specifically modified to match the angioarchitechtonica of the patient's brain.

The device for carrying out the method of the invention comprises a conventional three-way microcatheter device of the type shown in FIGS. 1 and 2, where FIG. 1 is a general view of a three-way catheter device used for realization of the method of the invention, and FIG. 2 is a view of a set of microcatheters for use with the device of FIG. 1 with some of the microcatheters having distal ends specifically modified to match the angioarchitechtonica of the patient's brain. In order to retain the specific shape in the free state of the catheter, the modified catheters have shape memory. More specifically, the device comprises a first or outer microcatheter 10 of a predetermined diameter that allows insertion of this microcatheter into the artery through the introducer (not shown), a second microcatheter 12 of a smaller diameter coaxially inserted into the first catheter 10 and at least a third microcatheter 13 inserted into the second catheter for advancement to the zone of interest in the bloodstream in the patient's brain. A plurality of such coaxial microcatheters may comprise up to six or more.

Reference numeral 14 designates a hemostatic valve at the proximal end of the outer catheter, 16 is a branched channel for injection of a physiological solution, 18 is a valve for connection to an injector of the physiological solution, and 20 designated a light-guiding optical-fiber device connected to a laser unit (not shown) for conducting the operation.

The microcatheter device of the invention is unique in that the number of microcatheters coaxially inserted one into the other may be as high as six or more and that the distal end of the innermost catheter 12 may be tailored to the specific and preliminarily determined angioarchitechtonica of the brain of the patient to be treated. Examples of such modified distal ends are shown in FIG. 2.

In the set of catheters 22, 24, 26, and 28 shown in FIG. 2, each catheter has different diameter for coaxial insertion. Reference numerals 22a, 24a, 26a, and 28a designate self-sealing hemostatic valves of the respective catheters. It can be seen that the distal ends 22b, 24b, 26b, 28b of the catheters 22, 24, 26, 28, and 30 have different shapes that are matched to the different shapes of the arteries into which the catheters must be inserted. In order to match the aforementioned specific profiles, the tips of the catheters have a shape memory.

Reference numerals 32 and 34 show examples of more intricate shapes of the innermost catheters.

EXAMPLE 1

Male Patient T., 56 years old, suffered for more than 2 years from evident derangement of memory and intellect, could not work, could not drive a vehicle, and was diagnosed with Altzheimer's disease.

The pre-operative examination included computerized tomography and magnetic resonance tomography of the brain, scintography, rheography, and brain angiography, which revealed involuntary changes accompanied by atrophy of the cerebral cortex in the frontal and parietal parts of the brain, abnormalities in the structure of the hippocampus, abnormalities in the blood circulation, abnormalities in pulse volume in the carotid sinuses, as well as reduction in the capillary phase of contrast enhancement in the frontoparietal areas with development of multiple arteriovenous shunts.

Endovascular laser intervention was carried out two years after manifestation of the disease symptomatic. The operation was carried out under carried under roentgenoscopy. Puncturing and catheterization were carried out in accordance with the Seldinger's technique. A 9 F introducer was installed, and a first 7 F guiding catheter was coaxially guided through the introducer and selectively inserted into the common femoral artery. A second 5 F modified guiding catheter was guided through the first catheter and positioned in a super-selective manner, first in the medial cerebral artery and then in the anterior cerebral artery. The second microcatheter, in turn, was used for insertion of a thin light-guiding optical-fiber device connected to a laser device. For subsequent laser treatment, the aforementioned light-guiding optical fiber device was guided to distal areas and to the affected portion of the microcirculation bloodstream. A light-guiding optical-fiber device was then coaxially inserted into the second guiding catheter and guided through and to the distal areas and to the affected area of the microcirculation bloodstream.

Laser treatment was carried out with the use of a low-energy laser with the power of 20 mW operating in a combined continuous-pulsed mode. The light-guiding optical-fiber device comprised a 2 F catheter with a 50 μm-diameter quartz-quartz type light-guide. Laser treatment was accompanied by introducing a heparinizated physiological solution with a dose of 0.1 ED heparin per 1 ml of the physiological solution at an introduction rate of 0.1 ml/sec.

After installation of the light-guiding optical-fiber device, the first guiding catheter was shifted and positioned in the descending arch of the aorta, and the second guiding catheter was also shifted and positioned in the proximal part of the common carotid artery. Following this, laser treatment was carried out by moving the light-guiding device together with the light-guide inside the blood vessel. A radio-opaque substance (OmniPak 350) was periodically introduced for X-ray TV control.

After operative intervention, the patient was subjected to a repeated cerebral angiography to evaluate the degree of regeneration of the blood passage through the microcirculation bloodstream.

The results showed that operation was successful, and the passage of blood through the endovascular capillary bloodstream was restored. The catheter and the introducer were extracted, hemostasis was carried out, and a compressive aseptic bandage was applied. The patient was transferred to a postoperative ward. A repeated scintography and REG showed normalization of the blood-circulation rate and pulse volume in the carotid sinuses. Two months later, the patient returned to work and was able to accomplish the work to full productivity.

He drove a car in Moscow approximately 100 to 200 km every day and returned to his normal full-value activities.

Seven months after the operation, the patient had a repeated computerized and magnetic-resonance tomography, the results of which showed significant improvement in the structure of the brain tissue.

EXAMPLE 2

Female patient P., 75 years old, suffered from a severe form of dementia, had mental and intellectual disorders, did not recognize relatives, did not remember events that just happened, and was diagnosed with Alzheimer's disease.

The patient was subjected to preoperative examination identical to the one described in Example 1. Operative endovascular laser intervention was conducted six years after manifestation of the disease symptomatic. The operation was carried out in the same sequence of operating steps as described in Example 1.

An 8 F introducer was installed, a first 7 F guiding catheter was coaxially guided through the introducer, and a second 5 F modified guiding catheter was guided through the first catheter.

Laser treatment was carried out with the use of a low-energy laser with the power of 20 mW operating in a combined continuous-pulsed mode. The light-guiding optical-fiber device comprised a 3 F catheter with a quartz-polymer type of light-guide having a diameter of 100 μm and an overall diameter of 400 μm. Laser treatment was accompanied by introducing a heparinizated physiological solution with a dose of 0.2 ED heparin per 1 ml of the physiological solution at an introduction rate of 0.15 ml/sec.

After operative intervention, the patient had a repeated cerebral angiography that showed regeneration of the blood passage through the microcirculation bloodstream and a decrease of arteriovenous shunts. The results of scintography and REG revealed normalization of the blood-circulation rate and pulse volume in the carotid sinuses.

Sometime later, the patient had a repeated computerized and magnetic-resonance tomography, the results of which showed significant improvement in the structure of the brain tissue.

Thus, it has been shown that the use of the method of the invention improves cerebral blood flow, provides improved rheographic characteristics in the carotid sinuses, and reduces involuntary changes in the brain tissues (according to computerized tomography), which, in turn, testifies to regenerative processes in the brain tissue and restoration of a patient's memory, thus making it possible to return the patient to his/her working activity and to improve the quality of life.

Thus, it has been shown that the invention provides a surgical method and apparatus for treating the Alzheimer's disease by restoring the microcirculation and collateral bloodstreams in the brain with regeneration of the surrounding brain tissue. The aforementioned treatment is carried out by removing plaque from the inner walls of the affected coronary blood vessels and thus improving the bloodstream flow to the affected and the surrounding areas. The method is carried out by means of a coaxial microcatheter device and with the use of a laser technique that restore the microcirculation and collateral bloodstreams in the brain.

Although the invention has been shown and described by way of specific examples, it is understood that various changes and modifications are possible with regard to materials, shapes, and dimensions, without departure from the scope of the patent claims. For example, the number of microcatheters in the assembly and the catheter shapes may exceed six and microcatheters may be different from those shown in the drawings. The microcatheters may be used for operations different from those described, e.g., for ablation of plaque deposited onto the inner walls of blood vessels. The blood vessels may be located in organs other than the brain. Different laser sources can be used for laser treatment. Methods other than those listed in the specification can be used for examining a patient's condition and results of laser intervention.

The invention claimed is:

1. An endovascular method of treating a patient suffering from Alzheimer's disease comprising the steps of:
    conducting preoperative examination of the patient for detecting changes that occurred in the patient's brain in connection with Alzheimer's disease and for defining angioarchitechtonica of the arteries and capillaries in the affected zone of the brain;
    providing a microcatheter device comprising at least a first channel and a second channel, a plurality of microcatheters of gradually reducing diameters for coaxial insertion one into another through the first channel, a light-guiding optical-fiber device connected to a low-power laser source and insertable into the innermost of said plurality of microcatheters, and a source of a washing liquid for the supply into the area being treated through the second channel;
    puncturing and catheterizing the common femoral artery of the patient for installing an introducer;
    inserting a first microcatheter of said plurality of microcatheters into the introducer;
    coaxially inserting and moving forward a second microcatheter of said plurality of microcatheters into the first microcatheter;
    coaxially inserting and moving forward a third microcatheter of said plurality of microcatheters into the second microcatheter;
    if necessary, sequentially inserting and moving forward other microcatheters of said plurality of microcatheters into the preceding microcatheter until reaching the affected zone of the microcirculation bloodstream in the patient's brain; inserting the light-guiding optical-fiber device coaxially into the innermost catheter of said plurality of microcatheters;
    guiding the light-guiding optical-fiber device to the affected zone through the innermost catheter; and
    restoring the circulation and collateral bloodstream in the brain with regeneration of the surrounding brain tissue by conducting laser treatment of the affected zone through a coronary blood vessel adjacent to the affected zone.

2. The method of claim 1, wherein the aforementioned microcatheters are made from a radio-opaque material and wherein said laser treatment is carried out under X-ray TV observation.

3. The method of claim 2, wherein the aforementioned laser has a power not less than 20 mW, said laser treatment being carried out in a mode selected from a continuous mode, pulsed mode, and a combined continuous-pulsed mode.

4. The method of claim 3, wherein the second microcatheter is coaxially inserted into the first microcatheter, the third microcatheter is inserted into the second microcatheter, and if necessary, other smaller-diameter microcatheters are sequentially inserted one into the other and moved forward to the medial cerebral artery or the anterior cerebral artery.

5. The method of claim 1, wherein said plurality of microcatheters are three to six microcatheters.

6. The method of claim 2, wherein said plurality of microcatheters are three to six microcatheters.

7. The method of claim 4, wherein said plurality of microcatheters are three to six microcatheters.

8. The method of claim 1, wherein said plurality of microcatheters have distal ends with a shape memorized by shape memory and wherein said shape corresponds to the angioarchitechtonica defined in said step of preoperative examination of the patient.

9. The method of claim 4, wherein said plurality of microcatheters have distal ends with a shape memorized by shape memory and wherein said shape corresponds to the angioarchitechtonica defined in said step of preoperative examination of the patient.

10. The method of claim 1, wherein the washing liquid is a heparinizated physiological solution.

11. The method of claim 4, wherein the washing liquid is a heparinizated physiological solution.

12. The method of claim 9, wherein the washing liquid is a heparinizated physiological solution.

13. The method of claim 1, wherein after inserting the light-guiding optical-fiber device coaxially into the innermost catheter of said plurality of microcatheters, the first catheter is shifted and positioned in the descending arch of the aorta, and the innermost catheter or several preceding catheters is/are shifted and positioned in the proximal part of the common carotid artery of the patient.

14. The method of claim 4, wherein after inserting the light-guiding optical-fiber device coaxially into the innermost catheter of said plurality of microcatheters, the first catheter is shifted and positioned in the descending arch of the aorta, and the innermost catheter or several preceding catheters is/are shifted and positioned in the proximal part of the common carotid artery of the patient.

15. The method of claim 9, wherein after inserting the light-guiding optical-fiber device coaxially into the innermost catheter of said plurality of microcatheters, the first catheter is shifted and positioned in the descending arch of the aorta, and the innermost catheter several preceding catheters is/are shifted and positioned in the proximal part of the common carotid artery of the patient.

16. The method of claim 12, wherein after inserting the light-guiding optical-fiber device coaxially into the innermost catheter of said plurality of microcatheters, the first catheter is shifted and positioned in the descending arch of the aorta, and the innermost catheter or several preceding catheters is/are shifted and positioned in the proximal part of the common carotid artery of the patient.

17. The method of claim 1, wherein the preoperative examination of the patient comprises computerized tomography and magnetic resonance tomography of the brain, scintography, rheography, and brain angiography for revealing involuntary changes accompanied by atrophy of the cerebral cortex in the frontal and parietal parts of the brain, abnormalities in the structure of the hippocampus, abnormalities in the blood circulation, abnormalities in pulse volume in carotid sinuses, as well as reduction in the capillary phase of contrast enhancement in the frontoparietal areas with development of multiple arteriovenous shunts.

* * * * *

UNITED STATES PATENT AND TRADEMARK OFFICE
CERTIFICATE OF CORRECTION

PATENT NO. : 7,389,776 B2
APPLICATION NO. : 11/650364
DATED : June 24, 2008
INVENTOR(S) : Ivan Vasilievich Maksimovich It is certified that error appears in the above-identified patent and that said Letters Patent is hereby corrected as shown below:

Title page, item [57] in the ABSTRACT, in lines 4 and 8, for the word "coronary", each occurrence, should read --cerebral--.
Column 3, line 57, for the word "scintography", should read --scintigraphy--.
Column 4, line 36, for the words "0.1 mk/sec", should read --0.1 ml/sec--.
Column 4, line 64, for the word "scintography", should read --scintigraphy--.
Column 5, line 20, for the word "vein", should read --artery--.
Column 5, line 56, for the words "0.1 mk/sec", should read --0.1 ml/sec--.
Column 6, line 24, for the word "scintography", should read --scintigraphy--.
Column 7, line 17, for the word "scintography", should read --scintigraphy--.
Column 8, line 3, for the word "scintography", should read --scintigraphy--.
Column 8, line 44, for the word "scintography", should read --scintigraphy--.
Column 8, line 64, for the word "coronary", should read --cerebral--.
In the CLAIMS, column 9, line 56, for the word "coronary", should read --cerebral--.
In the CLAIMS, column 10, lines 56, 57, for the word "scintography", should read --scintigraphy--.

Signed and Sealed this

Twenty-fifth Day of November, 2008

JON W. DUDAS
*Director of the United States Patent and Trademark Office*